United States Patent
Losso et al.

(10) Patent No.: US 10,376,566 B2
(45) Date of Patent: Aug. 13, 2019

(54) COMPOSITION AND METHOD FOR IMPROVING SLEEP DURATION AND QUALITY

(71) Applicants: Jack N. Losso, Baton Rouge, LA (US); Jose Daniel Estrada Andino, Baton Rouge, LA (US)

(72) Inventors: Jack N. Losso, Baton Rouge, LA (US); Jose Daniel Estrada Andino, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/625,777

(22) Filed: Jun. 16, 2017

(65) Prior Publication Data

US 2018/0021411 A1 Jan. 25, 2018

Related U.S. Application Data

(60) Provisional application No. 62/364,474, filed on Jul. 20, 2016.

(51) Int. Cl.
| | | |
|---|---|---|
| *A61K 38/00* | (2006.01) | |
| *A61K 38/39* | (2006.01) | |
| *A61K 31/198* | (2006.01) | |
| *A61K 31/728* | (2006.01) | |
| *A61K 31/353* | (2006.01) | |
| *A61K 31/191* | (2006.01) | |
| *A61K 31/343* | (2006.01) | |
| *A61K 36/28* | (2006.01) | |
| *A61K 31/28* | (2006.01) | |
| *A61K 31/365* | (2006.01) | |

(52) U.S. Cl.
CPC .............. *A61K 38/39* (2013.01); *A61K 31/191* (2013.01); *A61K 31/198* (2013.01); *A61K 31/28* (2013.01); *A61K 31/343* (2013.01); *A61K 31/353* (2013.01); *A61K 31/365* (2013.01); *A61K 31/728* (2013.01); *A61K 36/28* (2013.01)

(58) Field of Classification Search
None
See application file for complete search history.

(56) References Cited

U.S. PATENT DOCUMENTS

| | | | | |
|---|---|---|---|---|
| 2003/0091652 A1* | 5/2003 | Ishaq | ........... | A61K 35/32 424/548 |
| 2005/0164987 A1* | 7/2005 | Barberich | ......... | A61K 31/4045 514/58 |
| 2006/0134155 A1* | 6/2006 | Dryer | ........... | A61K 8/442 424/401 |
| 2009/0012155 A1* | 1/2009 | Kim | ........... | A61K 8/498 514/456 |
| 2013/0066048 A1* | 3/2013 | Raskin | ........... | A61K 36/48 530/350 |

OTHER PUBLICATIONS

Draths et al. J. Am. Chem. Soc. 1999, 121, p. 1603-1604.*
Street, R. et al., "*Cichorium intybus*: Traditional uses, phytochemistry, pharmacology, and toxicology," *Evidence-Based Complementary and Alternative Medicine*, vol. 2013, article ID 579319.
J. Barrett et al., "To sleep or not to sleep: A systematic review of the literature of pharmacological treatments of insomnia in children and adolescents with attention-deficit/hyperactivity disorder," *J. Child and Adolescent Psychopharmacology*, vol. 23, pp. 640-647 (2013).
M. Lyon et al., "The effects of L-theanine (Suntheanine® on objective sleep quality in boys with attention deficit hyperactivity disorder (ADHD): a randomized, double-blind, placebo-controlled clinical trial," *Alt. Med. Rev.*, vol. 16, pp. 348-354 (2011).
T. Rao, "In search of a safe natural sleep aid," *J. Am. Coll. Nutr.*, vol. 34, pp. 436-447 (2015).
M. Bannai et al., "New therapeutic strategy for amino acid medicine: Glycine improves the quality of sleep," *J. Pharmacol. Sci.*, vol. 118, pp. 145-148 (2012).
M. Bannai et al., "The effects of glycine on subjective daytime performance in partially sleep-restricted healthy volunteers," *Frontiers in Neurology*, vol. 3, article 61, 8 pages (2012).

* cited by examiner

*Primary Examiner* — Jeanette M Lieb
(74) *Attorney, Agent, or Firm* — John H. Runnels

(57) ABSTRACT

An intervention for sleep disorders comprises: collagen, a gelatin peptide, or the amino acid glycine; L-theanine; lactucopicrin, deoxylactucopicrin, or another lactucopicrin derivative; hyaluronic acid; epigallocatechin gallate; and quinic acid. The intervention helps regulate pro-inflammatory biomarkers that are often associated with insomnia development and progression. These biomarkers include cytokines and enzymes associated with tryptophan degradation. Inhibition of these enzymes and cytokines improves tryptophan availability and sleep quality, and allows individuals to sleep better with fewer side effects. The composition promotes high-quality, deep sleep.

5 Claims, 6 Drawing Sheets

H= histamine; E= EGCG; C= Chicory extract; Mep= Mepyramine

COMPOSITION AND METHOD FOR IMPROVING SLEEP DURATION AND QUALITY

The benefit of the Jul. 20, 2016 filing date of provisional patent application Ser. No. 62/364,474, the entire disclosure of which is incorporated by reference, is claimed under 35 U.S.C. § 119(e).

INTRODUCTION

Adequate sleep promotes health and the immune system. Sleep disorders and complaints can occur during childhood, adolescence or adult life [1, 2]. Insufficient sleep affects children's physical health as well as emotional, cognitive and social development. In the youth and adolescent age group, commonly encountered sleep disorders include insomnia, sleep-disordered breathing, parasomnias, and sleep disturbances associated with medical and psychiatric disorders. Insufficient sleep affects athletes' performance in many ways: it impairs reflexes, motivation, judgment, healing and even attention.

Sleep disturbances include insomnia, sleep apnea, sleep deprivation, restless legs syndrome, and sleep disorders resulting from chronic diseases such as diabetes, cancer, Parkinson's disease, Alzheimer's and others. Poor sleep disorders have negative influence on quality of life and are risk factors for the development of a myriad of chronic conditions including oxidative stress, pro-inflammation, fatigue, depression, obesity, metabolic syndrome, cardiovascular disease, and cancer. Sleep deprivation and disorders are common in Alzheimer's patients [3-5]. Sleep deprivation exacerbates several chronic disease conditions including inflammatory bowel diseases. Sleep disorders are associated with increased mortality [6]. Hypertension can predict the onset of sleep disorders, including insomnia and restless legs syndrome.

Chronic sleep shortage affects about 33% of the population in industrialized nations [7, 8] and 50% of older adults [2].

Insomnia is defined as a subjective complaint of difficulty initiating sleep, difficulty maintaining sleep, or early morning awakenings that occur at a minimum of 3 nights per week, for 3 months, and are associated with significant daytime consequences [9]. Examples of these daytime consequences include difficulty concentrating, mood disturbances, fatigue, and worry about sleep.

In older people, insomnia often is associated with other chronic conditions including physical and psychiatric ones. These conditions are more common among older women than older men [10]. In older people, the negative consequences of insufficient sleep include decreased quality of life, risk for falls, psychological and physical difficulties, economic and social costs, risk for nursing home placement, and increased mortality [2].

Many sleep disorders are inflammatory diseases. Cytokine levels play a role in normal sleep and sleep disturbances [11]. TNF-α and IL-1α are ubiquitous and pleiotropic, they often co-exist, and both have the capacity to induce each other and IL-6 [11]. TNF-α and IL-1β modulate normal physiology including normal sleep, the innate arm of the immune system, and inflammatory disease processes and progression [12, 13]. Both TNF-α and IL-1β are associated with sleep disorders such as narcolepsy [14-16], inflammatory bowel disease [17-19], ulcerative colitis [20], Crohn's disease [20-22], psoriasis [23, 24], Behçet's disease [25], arthritis [26, 27], amyotrophic lateral sclerosis [28], autoimmune diseases in general [29], fibromyalgia [30, 31], schizophrenia [32-34], illnesses that accompany malignancies [35], and central nervous system diseases such as multiple sclerosis [36, 37], and Parkinson's disease and Alzheimer's disease [38-40].

Presently-Used Approaches to Managing Insomnia

Currently, insomnia is managed by over-the-counter, non-prescription drugs such as melatonin or GABA; or by prescription drugs such as zolpidem (Ambien™) or Eszopiclone (Lunesta™). Melatonin is a naturally occurring hormone produced in the night to regulate circadian rhythms. Current reports suggest that melatonin is taken by adults and children about equally. Recent studies suggest, however, that the long-term safety of melatonin in children and adolescents is not known and that melatonin should not be used in this group [41]. Melatonin has been suggested to help children with autism [42]. Studies that have associated melatonin found in foods with health benefits may be flawed [43]. Drugs for insomnia have both beneficial effects [44] and side effects, sometimes serious side effects [45-48]. Insomnia can also be managed by tart cherry juice, which can be consumed at the level of 2 cups a day [49]. The high sugar content and cost of cherry juice limits its use by individuals with diabetes and consumers concerned with high sugar levels in foods.

A recent review of the efficacy of Zolpidem, L-theanine, and other compounds on insomnia in children with attention-deficit/hyperactivity disorder (ADHD) reported that both compounds "displayed a poor response in reducing sleep latency and increasing total sleep time, however L-theanine did produce an increase in sleep efficiency. Zolpidem produced high levels of side effects, leading to the largest dropout rate of all five studies. Clonidine reduced insomnia; and melatonin also exhibited a positive response, with reduced sleep latency, higher total sleep time, and higher sleep efficiency" [48]. The side effects of melatonin include headache, and theanine is a tranquilizer [50, 51].

R. Street et al., "*Cichorium intybus*: Traditional uses, phytochemistry, pharmacology, and toxicology," *Evidence-Based Complementary and Alternative Medicine*, vol. 2013, article ID 579319, 13 pages gives a review of traditional uses of chicory, its pharmacology, and related topics [52]. Chicory is used in traditional medicine, and is said to be useful for conditions ranging from uterine cancer, digestive disorders, high blood pressure, gout, malaria, stimulating appetite, gallstones, jaundice, liver diseases, and many others. Scientific studies have been conducted to investigate chicory's or its components' antibacterial activity, antihelmintic activity, antimalarial activity, hepatoprotective activity, antidiabetic activity, gastroprotective activity, anti-inflammatory activity, analgesic activity, antioxidant activity, tumor-inhibitory activity, antiallergic activity, and other activities.

J. Barrett et al., "To sleep or not to sleep: A systematic review of the literature of pharmacological treatments of insomnia in children and adolescents with attention-deficit/hyperactivity disorder," *J. Child and Adolescent Psychopharmacology*, vol. 23, pp. 640-647 (2013) reviews treatments that have been used in ADHD children and adolescents to treat insomnia, including Zolpidem, theanine, clonidine, and melatonin [48]. Theanine was reported to yield a poor response both in reducing sleep latency and in increasing total sleep time, although it did increase sleep efficiency and reduce nocturnal activity.

M. Lyon et al., "The effects of L-theanine (Suntheanine®) on objective sleep quality in boys with attention deficit hyperactivity disorder (ADHD): a randomized, double-blind, placebo-controlled clinical trial," *Alt. Med. Rev.*, vol. 16, pp. 348-354 (2011) reported that theanine improved sleep percentage and sleep efficiency in boys with ADHD [53]. A non-significant trend for less activity during sleep was observed. Sleep latency and other sleep parameters were unchanged.

T. Rao, "In search of a safe natural sleep aid," *J. Am. Coll. Nutr.*, vol. 34, pp. 436-447 (2015) reports that L-theanine has anxiolytic effects that promote quality of sleep [54].

M. Bannai et al., "New therapeutic strategy for amino acid medicine: Glycine improves the quality of sleep," *J. Pharmacol. Sci.*, vol. 118, pp. 145-148 (2012) reported that glycine induces a decrease in core body temperature, and that it improves subjective sleep quality [55]. See also M. Bannai et al., "The effects of glycine on subjective daytime performance in partially sleep-restricted healthy volunteers," *Frontiers in Neurology*, vol. 3, article 61, 8 pages (2012) [8].

Sleep disorders are becoming more common. The economic and social burden of sleep disorders is enormous. There is an unfilled need for improved methods for treating sleep disorders, with minimal side effects.

We have discovered an intervention for sleep disorders based on novel combinations of dietary bioactive compounds. The new intervention helps regulate pro-inflammatory biomarkers that are often associated with insomnia development and progression. These biomarkers include cytokines and enzymes associated with tryptophan degradation. Inhibition of these enzymes and cytokines improves tryptophan availability and sleep quality, and allows individuals to sleep better with fewer side effects. The novel composition promotes high-quality, deep sleep.

Bioactives Used in the Formulation

The combination of the present invention employs two or more; preferably three or more; more preferably four or more; and most preferably all of the following components: (1) Collagen peptides, i.e., peptides resulting from the partial hydrolysis of collagen, generally having a molecular weight less than 3,500 Dalton, preferably less than 2,000 Dalton and having a high level of glycine (see FIG. 1). The collagen may be derived from any convenient, economical source, for example beef collagen, porcine collagen, poultry collagen, or marine-source collagen. On an industrial scale, once a collagen source has been selected, enzymatic hydrolysis can be performed using single or multiple, specific or non-specific proteases. A heat pre-treatment may be applied to denature collagen into gelatin, which can likely be used as a source of "collagen peptides." Enzymes that may be used in the hydrolysis include, for example trypsin, alcalase, flavorzyme, pronase, pepsin, properase E, pronase, collagenase, bromelain Amano protease, and papain or a combination of these enzymes. Optional post-hydrolysis processing steps to obtain or concentrate bioactive peptides may include one or more of the following: ultrafiltration, dialysis, size-exclusion chromatography, and ion-exchange chromatography [56]. The resulting small, bioactive peptides (preferably of less than 2,000 Daltons) are rich in glycine, and some of the peptides may have antioxidative or anti-hypertensive activities [57-59]. To the inventors' knowledge, neither collagen nor collagen peptides nor glycine has previously been reported to reduce insomnia.

Collagen is high in glycine. Collagen peptides, rich in glycine, may help inhibit the angiotensin-converting enzyme, which can increase blood pressure [56]. Other sources rich in glycine may be used instead of, or in addition to the collagen peptides. Collagen is also low in phenylalanine, which is advantageous for phenylketonurics. The manner of making the peptides from collagen, such that they generally have a molecular weight less than 3,500 Dalton, preferably less than 2,000 Dalton is a matter of convenience, and may be carried out through any means known in the art. The peptides may optionally be denatured, e.g., peptides derived from gelatin. (2) High- or medium-weight hyaluronic acid (or hyaluronan), an optional ingredient, may play a role in promoting sleep due to its anti-inflammatory properties [60]. It is preferred to use the native hyaluronan, rather than its fragments. To the inventors' knowledge, hyaluronic acid has not previously been reported to have an effect on sleep. Preferably, the hyaluronic acid and the collagen peptides are both supplied in the same collagen peptide composition; hyaluronic acid is a naturally-occurring component of collagen. (3) Epigallocatechin gallate (EGCG), which inhibits enzymes associated with tryptophan degradation, and is preferably supplied as a tea extract, preferably a green tea extract, depleted in caffeine. EGCG can also be obtained separately from commercial sources. To the inventors' knowledge, ECGC has not previously been reported to have an effect on sleep. Green tea extracts high in ECGC and theanine are commercially available. (4) Theanine, which calms, is preferably supplied as a tea extract, preferably a green tea extract, depleted in caffeine. Preferably, the EGCG and theanine are both supplied in the same tea extract, preferably a green tea extract, depleted in caffeine. EGCG can also be obtained separately from commercial sources. (5) Lactucin and its derivative lactucopicrin have demonstrated excellent analgesic and sedative properties in an in vivo animal model [61]. Lactucin, its derivative deoxylactucin, lactucopicrin, or lactucopicrin derivatives (such as deoxylactucopicrin), or both, preferably supplied as a chicory extract (CE), most preferably a lightly-roasted chicory extract, or even raw chicory rich in inulin. We have found that longer roasting times deplete the desired components of CE, and that it is preferable to use a lighter, shorter roasting time than has typically been used for chicory employed as a coffee substitute or coffee flavoring agent. Longer roasting times are preferred when chicory is used as a coffee substitute or additive, because the product tastes unpleasantly bitter with shorter roasting times. The extract derived from light-roasted chicory is bitter and contains sesquiterpenes such as water-soluble lactucin and deoxylactucin, and very small amounts of relatively water-insoluble lactucopicrin and deoxylactucopicrin. Even though lactucopicrin has low solubility in water, it is very bitter even at low concentrations.) The preferred roasting temperature is 150-170° C., for 30 minutes or less. It is also possible to reduce or even omit the roasting step, to enhance the levels of lactucin, lactucopicrin and associated compounds, although the taste might then be objectionable to some consumers. To the inventors' knowledge, lactucin, lactucopicrin, and their derivatives have not previously been reported to have an effect on sleep. (6) Quinic acid. Quinic acid is preferably supplied as a chicory extract. Quinic acid can also be obtained separately from commercial sources. To the inventors' knowledge, quinic acid has not previously been reported to have an effect on sleep.

The combination is optionally flavored to enhance its palatability, preferably with natural flavoring agents.

Most of the components of the novel combination have not previously been reported to have an effect on sleep. In fact, to the inventors' knowledge, of all the components, only theanine has previously been associated with any effect on sleep. Further, there is a synergy, in that the effect of the combination is much greater than would be expected from the properties of the individual components.

The novel formulation enhances an early onset of sleep, and improves sleep depth, quality, and duration and reduces fatigue the next day. The formulation is also useful in reducing symptoms of sleep apnea. The combination possesses a synergy in these effects that is unmatched by any of the individual compounds, and that would not be expected from their individual properties. Indeed, none of the individual components alone has a strong effect on sleep onset, duration, or quality at all, although the novel combination does: (1) Collagen or gelatin peptides alone do not enhance sleep onset, depth, efficiency, or duration. The peptides alone do not improve sleep after awakening in the middle of the night. (2) EGCG alone does not enhance sleep onset, depth, efficiency, or duration. EGCG alone does not improve sleep after awakening in the middle of the night. (3) Theanine alone does not enhance sleep onset, depth, efficiency, or duration. Theanine alone does not improve sleep after awakening in the middle of the night. (4) CE alone does not enhance sleep onset, depth, efficiency, or duration. CE alone does not improve sleep after awakening in the middle of the night.

However, the novel combination of these components substantially enhances sleep onset, depth, efficiency, and duration; and improves sleep after awakening in the middle of the night. The novel combination also reduces sleepiness and fatigue the following day.

Based on preliminary reports from individuals who have tried various combinations (n=12, not statistically validated at this point), the most effective combination for providing deep and restful sleep was collagen peptide+hyaluronic acid+theanine+EGCG+Chicory extract; followed by collagen peptide+hyaluronic acid+theanine+Chicory extract; followed by Theanine+Glycine (free amino acid)+Chicory Extract.

EGCG inhibits Janus kinase 3, indoleamine dioxygenase, TNF-α, IL-6, IL-1α, and histamine, which may have an effect on improving sleep depth and quality. See the data reported below. To the inventors' knowledge, EGCG has not previously been reported to have an effect on sleep onset, efficiency, depth or duration.

Collagen peptides, rich in glycine, lower blood pressure and may lower body temperature. It is known that the free amino acid glycine can lower body temperature, and that body temperature is reduced during sleep. See Bannai and Kawai (2012) [55]. To the inventors' knowledge, similar effects with glycine-rich peptides have not been reported. Glycine does not, however, reduce awakening during the night.

CE is anti-oxidative, and is known to inhibit TNF-α [52]. Chicory is protective against oxidative stress by scavenging reactive oxygen species, boosting the endogenous antioxidant defense system, and by upregulating genes that encode antioxidant enzymes. See El-Sayed et al. (2015) [62]; Aquil et al. (2006) [63].

A series of in vitro tests were conducted, using levels of components that would be expected to approximate the concentrations that would be seen in vivo following oral consumption of 2 fluid ounces of the novel composition by a 70 kilogram individual.

Lab Results a. Inhibition of Janus Kinase 3 (Jak3) by EGCG, CE, or a Mixture of EGCG and CE.

Jak3 is expressed solely in immune cells. Jak3 expression is an upstream event for the activation of TNF-α and subsequent cytokines such as IL-6. HT-29 colon cancer cells in T-75 flasks were stimulated by LPS (control). HT-29 cells in T-75 flasks were also stimulated by LPS and treated with EGCG (Treatment 1=20 µM (E1), Treatment 2=35 µM (E2), or Treatment 3=50 µM (E3)), CE (extract from 3 g (C1), 6 g (C2), or 10 g (C3) of light roasted chicory), or combinations of the respective low, medium, and high concentrations of EGCG and CE (E1C1, E2C2, or E3C3). C1, C2, or C3 concentrations approximated the levels that would be expected following consumption of 2 fluid ounces of the novel composition by a 70 kilogram individual. C1, C2, and C3 were lyophilized and dissolved in the DMEM+10% FBS medium, filtered and added to the HT-29 cells and LPS in the medium. All treatments were in triplicates. Results are presented in FIG. 2. EGCG and CE both inhibited Jak3 expression in a dose-dependent manner, and the effect of the combination was synergistic.

b. Anti-Histamine Activity of EGCG, CE, or a Mixture of EGCG and CE.

HeLa cells were used as a model for determining the anti-histamine activity of EGCG, CE or the combination EGCG-CE. HeLa cells were treated with 1 µmol/L of histamine in absence (negative control) or presence of the EGCG at (Treatment 1=20 µM (E1), Treatment 2=35 µM (E2), or Treatment 3=50 µM (E3)) for 18 h. Histamine H1 receptor antagonist mepyramine maleate and histamine 4 receptor antagonist JNJ-7777120 were also used in separate treatments as positive controls. The effects of the treatments on histamine activity were determined by the inhibition of COX-2 expression. Results are presented in FIG. 3. EGCG inhibited COX-2 expression in a dose-dependent manner, although not as strongly as did the positive controls. CE also inhibited COX-2 levels although not as strongly as did mepyramine maleate or JNJ-7777120. The combination EGCG-CE synergistically inhibited COX-2.

c. Inhibition of TNF-α, IL-1α, and IL-6 by EGCG, CE, or a Mixture of EGCG and CE.

Supernatants from HT-29 cell cultures control or cell cultures treated with LPS were used to determine levels of TNF-α, IL-1β or IL-6 by ELISA. Supernatant was mixed with EGCG at (Treatment 1=20 µM (E1), Treatment 2=35 µM (E2), or Treatment 3=50 µM (E3)). The effective concentrations of TNF-α, IL-1β or IL-6 in supernatants were calculated using a standard curve developed using known standards of TNF-α, IL-1β or IL-6. Results are presented in FIGS. 4, 5, and 6, respectively. EGCG and CE each inhibited the activity of each of TNF-α, IL-1β and IL-6 in a dose-dependent manner; and the effect of the combination of EGCG and CE was synergistic and dose-dependent.

Without wishing to be bound by this hypothesis, we propose the following mechanism of action: Janus kinase enzyme occurs in a cascade upstream of the enzyme indoleamine dioxygenase; the latter degrades tryptophan, an amino acid associated with sleep. Inhibiting Janus 3 kinase down-regulates expression of indoleamine dioxygenase, which in turns decreases tryptophan degradation, and higher circulating levels of tryptophan enhance sleep. Further, there is an association between histamine levels and lack of sleep. Anti-histaminic compounds can also help individuals to fall asleep.

Formulations

Exemplary Formulations

Bacteria-free water is obtained by filtration or boiling. The bacteria-free water is mixed with the other ingredients in the preferred ranges: 0.5 to 12 g collagen peptide (or 0.5 to 5 g glycine as amino acid); 100 to 500 mg theanine (preferably as tea extract); 50 to 300 mg EGCG (preferably as tea extract); 1-10 g chicory extract. The mixture is optionally sweetened and flavored before serving. Nutritive or non-nutritive sweeteners known in the art may be added, such as sucrose, erythritol, or *stevia*. Flavorings known in the art may be added such as mocha, vanilla, caramel, hazelnut, peach, orange, pina colada, berries, and others. The final volume is brought to 60 ml and is then ready to serve. The nightly dose is about 60 mL. The solution has a shelf life of at least one year at room temperature, and longer if refrigerated. Nevertheless, for enhanced stability it is preferred to maintain the formulation as a powder until shortly before use. If the container in which the powder is stored is not well-sealed (or supplied with a separate desiccant), the powder can absorb moisture in a humid environment. The liquid can be susceptible to mold or yeast growth, unless pasteurized and stored in a sealed container. The formulation may be presented as a 30-60 mL (1-2 fluid ounce) beverage, or as a dried powder or tablet.

A preferred method for preparing the formulation is to percolate hot water through the source materials. We found that percolation works better than brewing, presumably because the effective contact time between the water and the components is greater. Surprisingly, we found that using filter paper (as might be used in brewing) is undesirable; the filter paper evidently absorbs at least some of the active ingredients. Perhaps small suspended particles are important; or perhaps the fibers of the paper adsorb active compounds. In a future experiment (not yet carried out) we will test an inert filter, such as a commercially-available gold-plated coffee filter.

The liquid or dry formulation is shelf-stable for at least one year at room temperature, if properly sealed. Optionally, stability may be enhanced by adding stabilizers known in the art, for example cultured dextrose or potassium sorbate.

Preparation of Chicory Extract (CE) Powder

Raw or lightly roasted chicory roots (3 to 10 g) are ground, and then percolated for 15-50 min in five to ten times their volume in water, filtered, cooled, and spray-dried with 15-35% low dextrose equivalent (DE) maltodextrin or tricalcium phosphate. Other methods of drying can be used, for example lyophilization, but spray-drying is preferred. Percolation is a preferred method to extract the chicory roots. Brewing can also be used. The dried powder is rich in bitter sesquiterpenes such as lactucin, lactucopicrin, and their derivatives; inulin; pectin; quinic acid; chicoric acid; and chlorogenic acid. Cf. U.S. patent application publication no. US20160095337A1, for the preparation of low-bitter chicory products.

The spray dried powder can be used in formulations including not only formulations for managing insomnia, but also for managing or ameliorating other conditions such as Parkinson's disease, inflammatory bowel disease, multiple sclerosis, arthritis, diabetes, atherosclerosis, cancer, obesity, autism, ADHD, Alzheimer's, fibromyalgia, sleep apnea, and insulin resistance.

Anecdotal Sleep Reports

A 7-day anecdotal sleep study was performed with 14 patients.

Other anecdotal sleep studies have been carried on for less than 7 days by over 40 additional individuals, and they have reported generally similar results.

Fourteen patients were provided a 7-day dose of the sleep formulation; they logged their observations and reported them. Following are selected extracts from their self-reported observations:

Participant #1
Slept well through the night, no stress. A little bit of migraine but I took care of it.

Participant #2
I have slept better than usual this week. Even when I woke up after 1:00 a.m. was able to go back to sleep until the morning and go to work without feeling tired and sleepy.

Participant #3
For the entire week I took the beverage 1-2 hours before bedtime, I slept better than before. I woke up but was able to get back to sleep faster.

Participant #4
I wake a little less. Seemed to fall back asleep quicker and sleep longer. Seem to remember dreams much better.

Participant #5
I am less sleepy in the mornings than I was before (even when going to bed at the same time). My sleep quality was better than before.

Participant #6
I feel like I am sleeping better with this product.

Participant #7
I go to bed at 9:00 p.m., and typically wake up at 1:00 a.m. and never go back to sleep until I drive to work in the morning. This beverage helped me a bit. I was still waking up at 1:00 a.m. or 2:00 a.m. but was able to sleep again, wake up in the morning and have a better day than before taking this beverage.

Participant #9
Slept better than usual, woke up sometimes at night, but did go back to sleep. It was not perfect but better than before when I could just not fall asleep at all.

Participant #10
Worked better than chamomile. I could sleep better and not feel sleepy during the day.

Participant #11
Sleep is a problem for me. I tried this formulation and on night one I was sleeping better than ever before. Can you make 10 gallons? How much will you charge?

Participant #12
This male has a hard time sleeping. He tried it, slept very well, woke up around 1 a.m. but was able to go back to sleep again.

Participant #13
I like the stuff. I slept very well and will use it again.

Participant #14
Please send me a 2-week serving because I am sleeping better.

Results from another preliminary study are summarized in Table 1:

TABLE 1

Effect of sleep-aid formulation with E3 and C3 on Subjective Sleep Quality in 56 volunteer participants with sleep problems

| Question Number | Question | Response |
|---|---|---|
| 1 | How difficult was it to fall asleep after taking the sleep formulation? | Not difficult (96%) |
| 2 | How long did it take you to fall asleep? | Within 30 min (96%) |
| 3 | How deep was your sleep? | Very deep (96%) |

TABLE 1-continued

Effect of sleep-aid formulation with E3 and C3 on Subjective Sleep Quality in 56 volunteer participants with sleep problems

| Question Number | Question | Response |
|---|---|---|
| 4 | How often did you wake up at night? | As usual (100%) |
| 5 | Did you return to sleep after awakening in the middle of the night? | Yes (100%) |
| 6 | Was it easy to wake up in the morning after taking the sleep formulation? | Yes (100%) |
| 7 | How was your day compared to days after taking other sleep aids? | Better (96%) |
| 8 | Did you feel daytime sleepiness after a night with the sleep formulation? | Not at all (100%) |
| 9 | Did you feel any headache or side effect after taking the sleep formulation? | No (100%) |
| 10 | Overall, how satisfied were you with the sleep formulation? | Very (96%) |

As used herein, an "effective amount" of a composition refers to a quantity of the composition sufficient to be effective to enhance the duration, quality, or onset of sleep to a clinically significant degree; or alternatively, to a statistically significant degree as compared to control. "Statistical significance" means significance at the $P<0.05$ level, or such other measure of statistical significance as would be used by those of skill in the art of biomedical statistics in the context of the treatment. An "effective amount" can vary with the age, general condition of the subject, the severity of the condition being treated, the duration of the treatment, the nature of any concurrent treatment, the pharmaceutically acceptable carrier used, and like factors within the knowledge and expertise of those skilled in the art. As appropriate, an "effective amount" in any individual case can be determined by routine experimentation.

The complete disclosures of all references cited in this application are hereby incorporated by reference. In the event of an otherwise irreconcilable conflict, however, the present specification shall control.

EMBODIMENTS (SET A)

1. A composition comprising at least two of three Components selected from the group consisting of: (Component 1) Collagen or gelatin peptides or glycine amino acid having a molecular weight less than 3500 Dalton, preferably less than 2000 Dalton; (Component 2) L-Theanine; and (Component 3) Lactucopicrin or lactucopicrin derivatives, such as lactucopicrin or deoxylactucopicrin.

2. The composition of Embodiment 1, additionally comprising at least one additional Component selected from the group consisting of: (Component 4) hyaluronic acid, (Component 5) epigallocatechin gallate, and (Component 6) quinic acid.

3. The composition of Embodiment 1, wherein said composition comprises each of Component 1, Component 2, and Component 3.

4. The composition of Embodiment 3, additionally comprising at least one Component selected from the group consisting of: (Component 4) hyaluronic acid, (Component 5) epigallocatechin gallate, and (Component 6) quinic acid.

5. The composition of Embodiment 4, wherein said composition comprises each of Component 4, Component 5, and Component 6.

6. The composition of Embodiment 5, wherein said composition comprises extract of tea (*Camellia sinensis*) and extract of chicory (*Cichorium intybus*).

7. The composition of Embodiment 1, additionally comprising water, a nutritive or non-nutritive sweetener, and a flavoring agent; wherein said flavoring agent is not one of said Components.

8. The composition of Embodiment 2, additionally comprising water, a nutritive or non-nutritive sweetener, and a flavoring agent; wherein said flavoring agent is not one of said Components.

9. The composition of Embodiment 3, additionally comprising water, a nutritive or non-nutritive sweetener, and a flavoring agent; wherein said flavoring agent is not one of said Components.

10. The composition of Embodiment 4, additionally comprising water, a nutritive or non-nutritive sweetener, and a flavoring agent; wherein said flavoring agent is not one of said Components.

11. The composition of Embodiment 5, additionally comprising water, a nutritive or non-nutritive sweetener, and a flavoring agent; wherein said flavoring agent is not one of said Components.

12. The composition of Embodiment 6, additionally comprising water, a nutritive or non-nutritive sweetener, and a flavoring agent; wherein said flavoring agent is not one of said Components.

13. A method for improving the symptoms of a sleep disorder in a human, said method comprising administering to the human an effective amount of the composition of Embodiment 1.

14. A method for improving the symptoms of a sleep disorder in a human, said method comprising administering to the human an effective amount of the composition of Embodiment 2.

15. A method for improving the symptoms of a sleep disorder in a human, said method comprising administering to the human an effective amount of the composition of Embodiment 3.

16. A method for improving the symptoms of a sleep disorder in a human, said method comprising administering to the human an effective amount of the composition of Embodiment 4.

17. A method for improving the symptoms of a sleep disorder in a human, said method comprising administering to the human an effective amount of the composition of Embodiment 5.

18. A method for improving the symptoms of a sleep disorder in a human, said method comprising administering to the human an effective amount of the composition of Embodiment 6.

19. A method for improving the symptoms of a sleep disorder in a human, said method comprising administering to the human an effective amount of the composition of Embodiment 7.

20. A method for improving the symptoms of a sleep disorder in a human, said method comprising administering to the human an effective amount of the composition of Embodiment 8.

21. A method for improving the symptoms of a sleep disorder in a human, said method comprising administering to the human an effective amount of the composition of Embodiment 9.

22. A method for improving the symptoms of a sleep disorder in a human, said method comprising administering to the human an effective amount of the composition of Embodiment 10.

23. A method for treating the symptoms of a sleep disorder in a human, said method comprising administering to the human an effective amount of the composition of Embodiment 11.

24. A method for treating the symptoms of a sleep disorder in a human, said method comprising administering to the human an effective amount of the composition of Embodiment 12.

EMBODIMENTS (SET B)

1. A composition comprising at least two Components selected from the group consisting of: (Component 1) Collagen or gelatin peptides having a molecular weight less than 3500 Dalton, preferably less than 2000 Daltons, or glycine amino acid (0.5-12 g); (Component 2) L-Theanine (100-500 mg); and (Component 3) lactucin (0.2 mg-2.0 mg), Lactucopicrin (0.05 mg-0.2 mg) or their derivatives including 8-deoxylactucin (0.05 mg-0.2 mg), 11,13-dihydrolactucin (0.1-0.5 mg), and 11,13-dihydrolactucopicrin (0.05 mg-0.1 mg). Higher levels of these bitter compounds can be obtained by extended brewing/percolation times, e.g., more than 50 min.

2. The composition of Embodiment 1, additionally comprising at least one Component selected from the group consisting of: (Component 4) hyaluronic acid (4-150 mg), (Component 5) epigallocatechin gallate (100-300 mg), and (Component 6) quinic acid (5-15 mg).

3. The composition of Embodiment 1, wherein said composition comprises Component 1, Component 2, and Component 3.

4. The composition of Embodiment 3, additionally comprising at least one Component selected from the group consisting of: (Component 4) hyaluronic acid, (Component 5) epigallocatechin gallate, and (Component 6) quinic acid.

5. The composition of Embodiment 4, wherein said composition comprises Component 4, Component 5, and Component 6.

6. The composition of Embodiment 5, wherein said composition comprises extract of tea (*Camellia sinensis*) and extract of chicory (*Cichorium intybus*).

7. The composition of Embodiment 1, additionally comprising water, a nutritive or non-nutritive sweetener, and a flavoring agent; wherein said flavoring agent is not one of said Components.

8. The composition of Embodiment 2, additionally comprising water, a nutritive or non-nutritive sweetener, and a flavoring agent; wherein said flavoring agent is not one of said Components.

9. The composition of Embodiment 3, additionally comprising water, a nutritive or non-nutritive sweetener, and a flavoring agent; wherein said flavoring agent is not one of said Components.

10. The composition of Embodiment 4, additionally comprising water, a nutritive or non-nutritive sweetener, and a flavoring agent; wherein said flavoring agent is not one of said Components.

11. The composition of Embodiment 5, additionally comprising water, a nutritive or non-nutritive sweetener, and a flavoring agent; wherein said flavoring agent is not one of said Components.

12. The composition of Embodiment 6, additionally comprising water, a nutritive or non-nutritive sweetener, and a flavoring agent; wherein said flavoring agent is not one of said Components.

13. A method for improving the symptoms of a sleep disorder in a human, said method comprising administering to the human an effective amount of the composition of Embodiment 1; preferably 1 to 2 fluid ounces, preferably 2 fluid ounces.

14. A method for improving the symptoms of a sleep disorder in a human, said method comprising administering to the human an effective amount of the composition of Embodiment 2.

15. A method for improving the symptoms of a sleep disorder in a human, said method comprising administering to the human an effective amount of the composition of Embodiment 3.

16. A method for improving the symptoms of a sleep disorder in a human, said method comprising administering to the human an effective amount of the composition of Embodiment 4.

17. A method for improving the symptoms of a sleep disorder in a human, said method comprising administering to the human an effective amount of the composition of Embodiment 5.

18. A method for improving the symptoms of a sleep disorder in a human, said method comprising administering to the human an effective amount of the composition of Embodiment 6.

19. A method for improving the symptoms of a sleep disorder in a human, said method comprising administering to the human an effective amount of the composition of Embodiment 7.

20. A method for improving the symptoms of a sleep disorder in a human, said method comprising administering to the human an effective amount of the composition of Embodiment 8.

21. A method for managing the symptoms of a sleep disorder in a human, said method comprising administering to the human an effective amount of the composition of Embodiment 9.

22. A method for managing the symptoms of a sleep disorder in a human, said method comprising administering to the human an effective amount of the composition of Embodiment 10.

23. A method for managing the symptoms of a sleep disorder in a human, said method comprising administering to the human an effective amount of the composition of Embodiment 11.

24. A method for managing the symptoms of a sleep disorder in a human, said method comprising administering to the human an effective amount of the composition of Embodiment 12.

LITERATURE CITED

Figure 1:
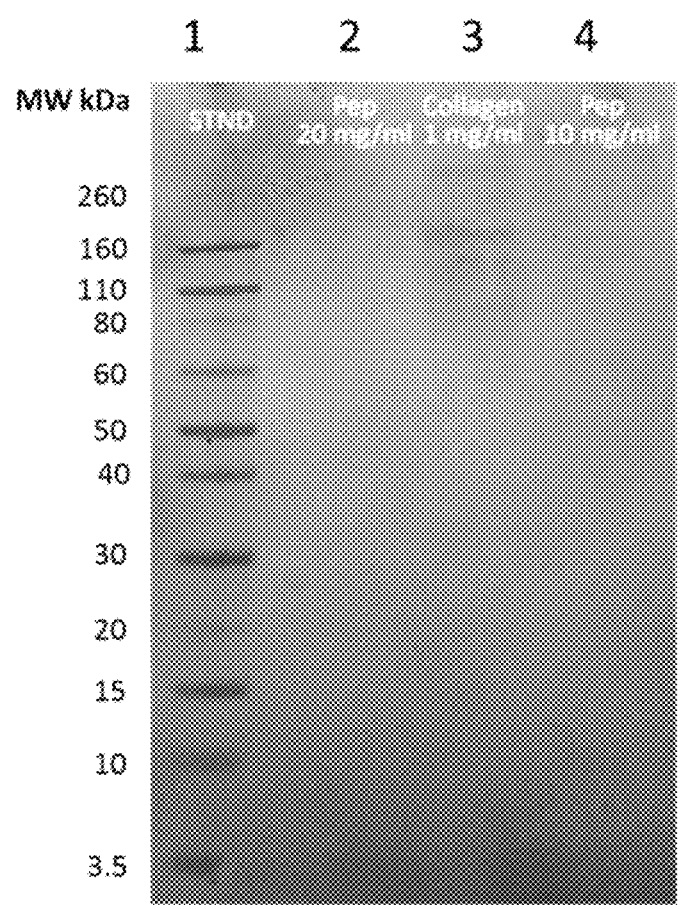
FIG. 1: Gel electrophoresis of collagen and collagen peptides to determine the approximate size of the collagen peptides. Lane 1 had a mixture molecular weight markers/ standards (STND) to determine the approximate sizes of other protein or peptide molecule(s) on the gel. In lane 2, 20 mg of collagen peptides were loaded and separated by electrophoresis. No peptides were seen larger than 3.5 kDa. Lane 3 contained collagen at 1 mg/ml. The band above 160 kDa showed the presence of collagen before hydrolysis. Lane 4 contained collagen peptides at 10 mg/ml. Similar to lane 2, there were no peptides larger than 3.5 kDa. Lane 2 contained twice the amount of collagen that was loaded in Lane 4. The results showed that the mixture contained no peptides higher than 3.5 kDa.
Figure 2:
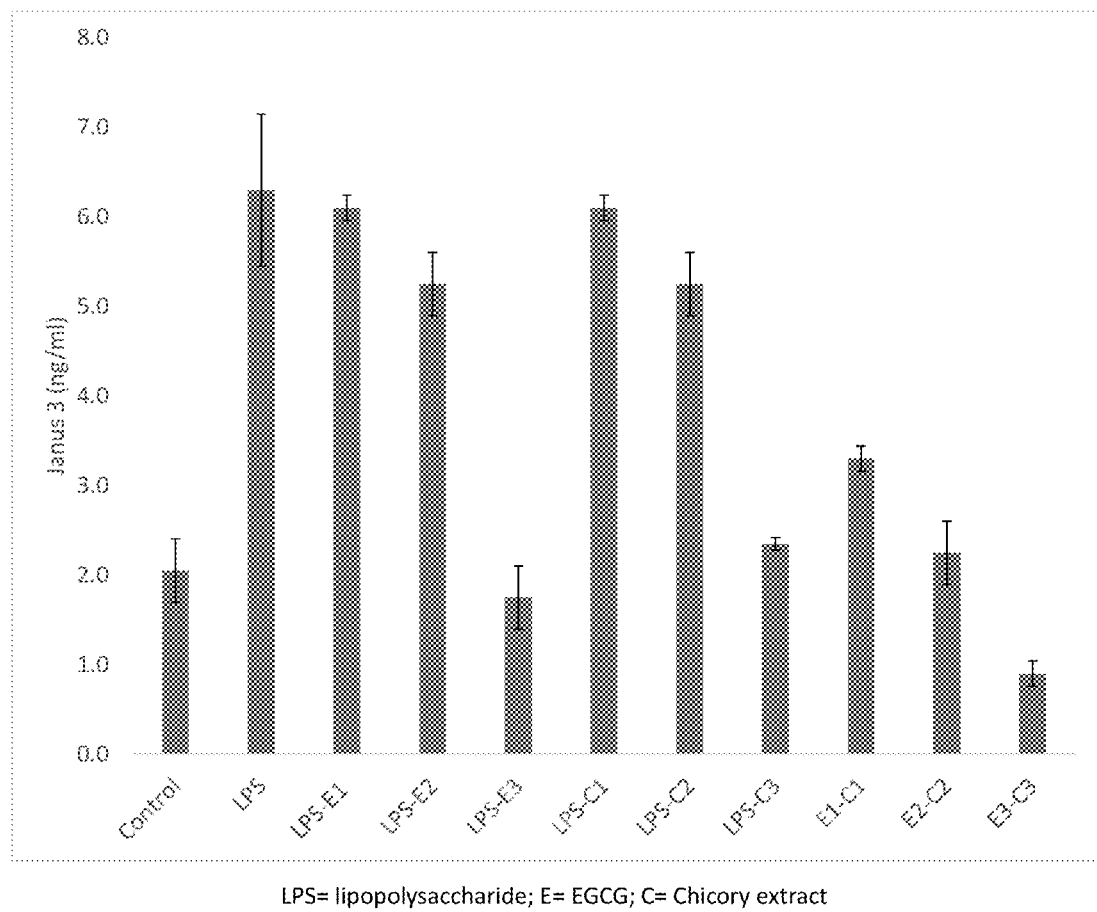
FIG. 2: Inhibition of JAK3 kinase by green tea EGCG. Effect of EGCG at different concentrations, chicory extract (C) at different concentrations, or the combination of EGCG and chicory extract (E-C) at different concentrations on JAK3 kinase levels in HT-29 cell culture treated with LPS.
Figure 3:
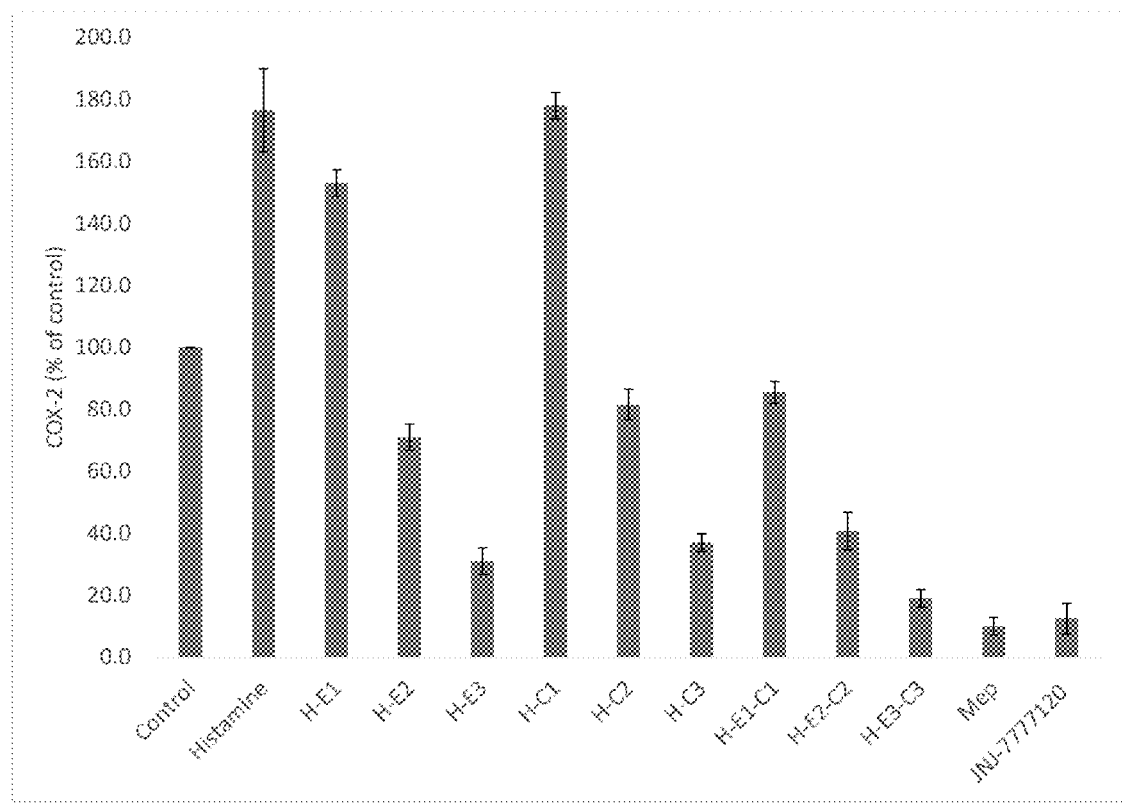
FIG. 3: Effect of EGCG at different concentrations, chicory extract (C) at different concentrations, or the combination of EGCG and chicory extract (E-C) at different concentrations on COX-2 levels in HeLa cell culture treated with LPS. Comparison was made with mepyramine maleate as histamine H1 receptor antagonist as positive control. Comparison was also made with histamine 4 receptor antagonist JNJ-7777120 as positive control.
Figure 4:
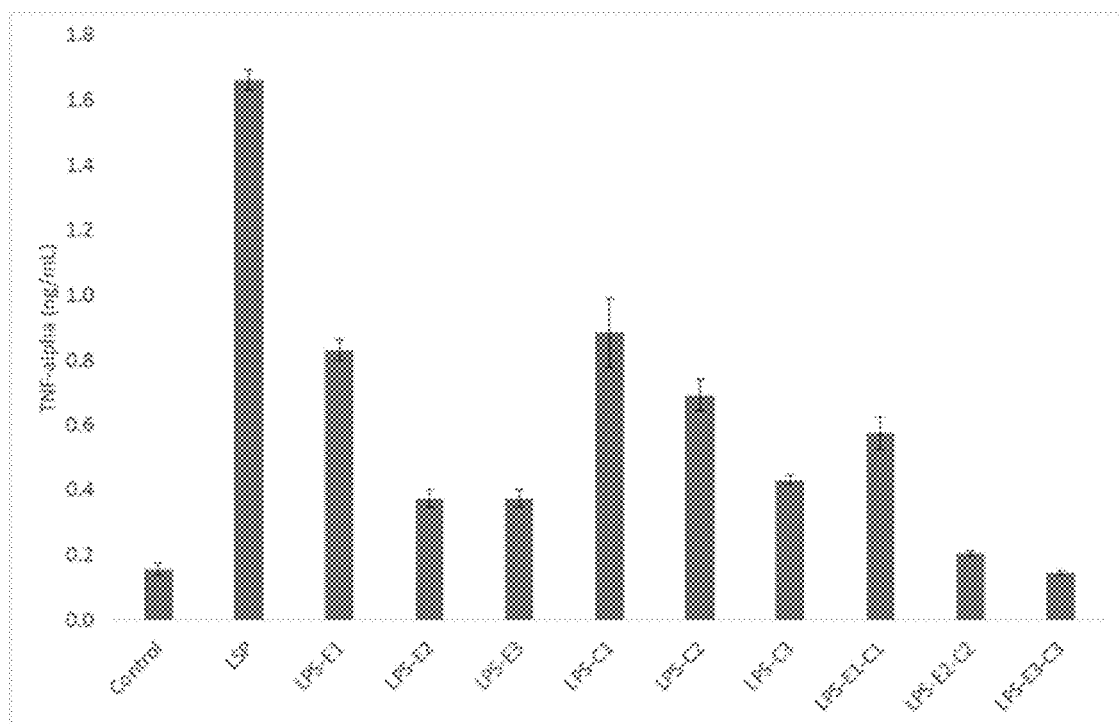
FIG. 4. Effect of EGCG at different concentrations, chicory extract (C) at different concentrations, or the combination of EGCG and chicory extract (E-C) at different concentrations on TNF-alpha levels in HT-29 cell culture treated with LPS.
Figure 5:
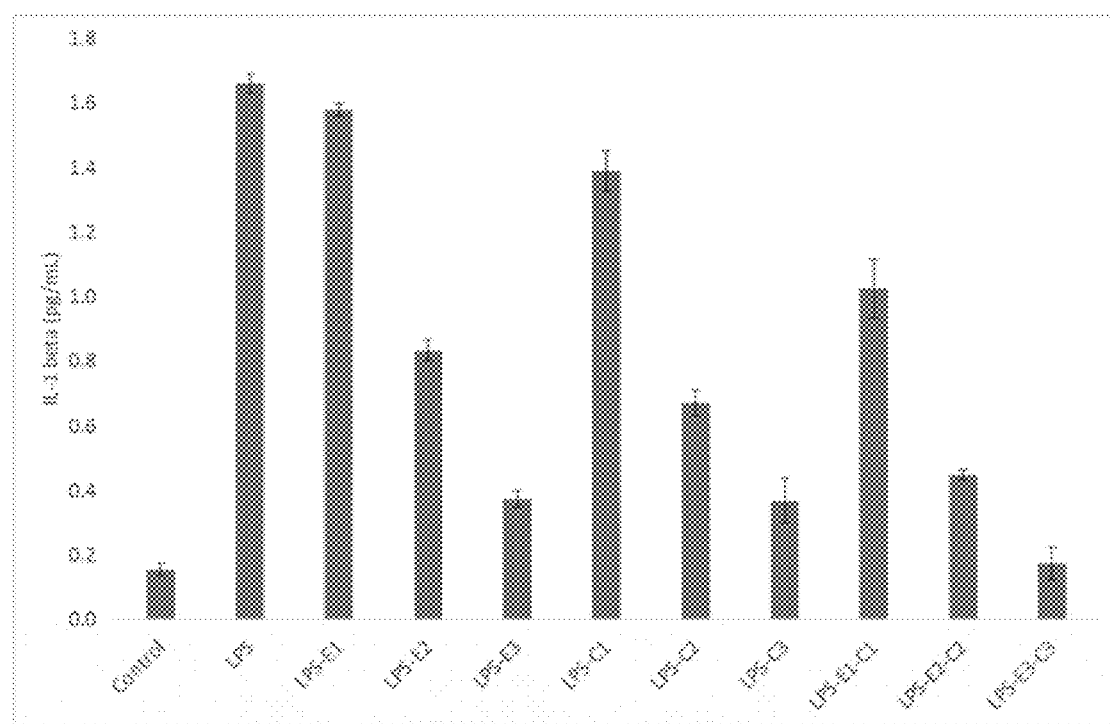
FIG. 5: Effect of EGCG at different concentrations, chicory extract (C) at different concentrations, or the combination of EGCG and chicory extract (E-C) at different concentrations on IL-1β levels in HT-29 cell culture treated with LPS.
Figure 6:
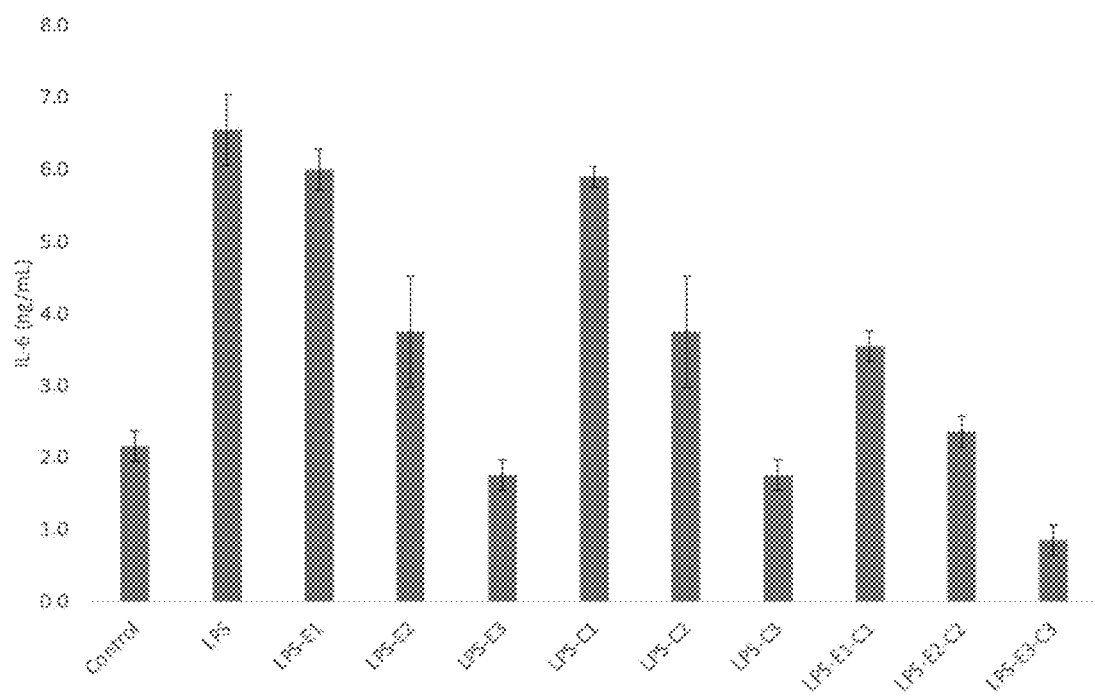
FIG. 6: Effect of EGCG at different concentrations, chicory extract (C) at different concentrations, or the combination of EGCG and chicory extract (E-C) at different concentrations on IL-6 levels in HT-29 cell culture treated with LPS.

[1] Baweja R, Calhoun S, Singareddy R. Sleep problems in children. Minerva pediatrica 2013; 65:457-472.
[2] Rodriguez J C, Dzierzewski J M, Alessi C A. Sleep problems in the elderly. The Medical clinics of North America 2015; 99:431-439.
[3] Beaulieu-Bonneau S, Hudon C. Sleep disturbances in older adults with mild cognitive impairment. International psychogeriatrics/IPA 2009; 21:654-666.
[4] Cochen V, Arbus C, Soto M E et al. Sleep disorders and their impacts on healthy, dependent, and frail older adults. The journal of nutrition, health & aging 2009; 13:322-329.
[5] Vecchierini M F. [Sleep disturbances in Alzheimer's disease and other dementias]. Psychologie & neuropsychiatrie du vieillissement 2010; 8:15-23.
[6] Grandner M A. Addressing sleep disturbances: an opportunity to prevent cardiometabolic disease? Int Rev Psychiatry 2014; 26:155-176.
[7] Terzano M G, Rossi M, Palomba V et al. New drugs for insomnia: comparative tolerability of zopiclone, zolpidem and zaleplon. Drug safety 2003; 26:261-282.
[8] Bannai M, Kawai N, Ono K et al. The effects of glycine on subjective daytime performance in partially sleep-restricted healthy volunteers. Frontiers in neurology 2012; 3:61.
[9] Rodriguez J C, Dzierzewski J M, Alessi C A. Sleep Problems in the Elderly. Medical Clinics of North America 2014.
[10] Krishnan V, Collop N A. Gender differences in sleep disorders. Current opinion in pulmonary medicine 2006; 12:383-389.
[11] Clark I A, Vissel B. Inflammation-sleep interface in brain disease: TNF, insulin, orexin. Journal of neuroinflammation 2014; 11:51.
[12] Krueger J M, Clinton J M, Winters B D et al. Involvement of cytokines in slow wave sleep. Progress in brain research 2011; 193:39-47.
[13] Mullington J M, Simpson N S, Meier-Ewert H K, Haack M. Sleep loss and inflammation. Best practice & research. Clinical endocrinology & metabolism 2010; 24:775-784.
[14] Himmerich H, Beitinger P A, Fulda S et al. Plasma levels of tumor necrosis factor alpha and soluble tumor necrosis factor receptors in patients with narcolepsy. Archives of internal medicine 2006; 166:1739-1743.
[15] Chrousos G, Vgontzas A N, Kritikou I. HPA Axis and Sleep. In: Endotext. Edited by: De Groot U, Beck-Peccoz P, Chrousos G et al. South Dartmouth (M A): 2000.
[16] Tanaka S, Honda M, Toyoda H, Kodama T. Increased plasma IL-6, IL-8, TNF-alpha, and G-CSF in Japanese narcolepsy. Human immunology 2014; 75:940-944.
[17] Koutroubakis I E, Ramos-Rivers C, Regueiro M et al. The Influence of Anti-tumor Necrosis Factor Agents on Hemoglobin Levels of Patients with Inflammatory Bowel disease. Inflammatory bowel diseases 2015.
[18] Jiang W, Li X. Molecular Analysis of Inflammatory Bowel Disease: Clinically Useful Tools for Diagnosis, Response Prediction, and Monitoring of Targeted Therapy. Molecular diagnosis & therapy 2015.
[19] Ali T, Orr W C. Sleep disturbances and inflammatory bowel disease. Inflammatory bowel diseases 2014; 20:1986-1995.
[20] Lahad A, Weiss B. Current therapy of pediatric Crohn's disease. World journal of gastrointestinal pathophysiology 2015; 6:33-42.
[21] van Dullemen H M, van Deventer S J, Hommes D W et al. Treatment of Crohn's disease with anti-tumor necrosis factor chimeric monoclonal antibody (cA2). Gastroenterology 1995; 109:129-135.
[22] Randall C W, Vizuete J A, Martinez N et al. From historical perspectives to modern therapy: a review of current and future biological treatments for Crohn's disease. Therapeutic advances in gastroenterology 2015; 8:143-159.
[23] Chaudhari U, Romano P, Mulcahy L D et al. Efficacy and safety of infliximab monotherapy for plaque-type psoriasis: a randomised trial. Lancet 2001; 357:1842-1847.
[24] Mitsui A, Tada Y, Takahashi T et al. Serum IL-33 levels are increased in patients with psoriasis. Clinical and experimental dermatology 2015.
[25] Caso F, Costa L, Rigante D et al. Biological treatments in Behcet's disease: beyond anti-TNF therapy. Mediators of inflammation 2014; 2014:107421.
[26] Paramarta J E, Baeten D, De Rycke L. Synovial Tissue Response to Treatment with TNF Blockers in Peripheral Spondyloarthritis. The open rheumatology journal 2011; 5:127-132.

[27] Elliott M J, Maini R N, Feldmann M et al. Randomised double-blind comparison of chimeric monoclonal antibody to tumour necrosis factor alpha (cA2) versus placebo in rheumatoid arthritis. Lancet 1994; 344:1105-1110.

[28] Kiaei M, Petri S, Kipiani K et al. Thalidomide and lenalidomide extend survival in a transgenic mouse model of amyotrophic lateral sclerosis. The Journal of neuroscience: the official journal of the Society for Neuroscience 2006; 26:2467-2473.

[29] Wang D, Li Y, Liu Y, Shi G. The Use of Biologic Therapies in the Treatment of Rheumatoid Arthritis. Current pharmaceutical biotechnology 2014; 15:542-548.

[30] Togo F, Natelson B H, Adler G K et al. Plasma cytokine fluctuations over time in healthy controls and patients with fibromyalgia. Exp Biol Med (Maywood) 2009; 234: 232-240.

[31] Bazzichi L, Rossi A, Massimetti G et al. Cytokine patterns in fibromyalgia and their correlation with clinical manifestations. Clinical and experimental rheumatology 2007; 25:225-230.

[32] Suvisaari J, Loo B M, Saarni S E et al. Inflammation in psychotic disorders: a population-based study. Psychiatry Res 2011; 189:305-311.

[33] Dean B, Gibbons A S, Tawadros N et al. Different changes in cortical tumor necrosis factor-alpha-related pathways in schizophrenia and mood disorders. Molecular psychiatry 2013; 18:767-773.

[34] Song X Q, Chen X M, Zhang W et al. [Study of adiponectin, IL-1beta, IL-6 and TNF-alpha in first episode drug nasmall yi, Ukrainianve schizophrenia]. Zhonghua yi xue za zhi 2013; 93:3256-3260.

[35] Oliff A, Defeo-Jones D, Boyer M et al. Tumors secreting human TNF/cachectin induce cachexia in mice. Cell 1987; 50:555-563.

[36] Ramirez-Ramirez V, Macias-Islas M A, Ortiz G G et al. Efficacy of fish oil on serum of TNF alpha, IL-1 beta, and IL-6 oxidative stress markers in multiple sclerosis treated with interferon beta-1b. Oxidative medicine and cellular longevity 2013; 2013:709493.

[37] Wen S R, Liu G J, Feng R N et al. Increased levels of IL-23 and osteopontin in serum and cerebrospinal fluid of multiple sclerosis patients. Journal of neuroimmunology 2012; 244:94-96.

[38] Adibhatla R M, Hatcher J F. Altered lipid metabolism in brain injury and disorders. Sub-cellular biochemistry 2008; 49:241-268.

[39] Singhal G, Jaehne E J, Corrigan F et al. Inflammasomes in neuroinflammation and changes in brain function: a focused review. Frontiers in neuroscience 2014; 8:315.

[40] Rubio-Perez J M, Morillas-Ruiz J M. A review: inflammatory process in Alzheimer's disease, role of cytokines. The Scientific World Journal 2012; 2012:756357.

[41] Kennaway D J. Potential safety issues in the use of the hormone melatonin in paediatrics. Journal of paediatrics and child health 2015; 51:584-589.

[42] Klein N, Kemper K J. Integrative approaches to caring for children with autism. Current problems in pediatric and adolescent health care 2016.

[43] Kennaway D J. Are the proposed benefits of melatonin-rich foods too hard to swallow? Crit Rev Food Sci Nutr 2015:0.

[44] Monti J M, Pandi-Perumal S R. Eszopiclone: its use in the treatment of insomnia. Neuropsychiatric disease and treatment 2007; 3:441-453.

[45] MacFarlane J, Morin C M, Montplaisir J. Hypnotics in insomnia: the experience of zolpidem. Clin Ther 2014; 36:1676-1701.

[46] Singh H, Thangaraju P, Natt N K. Sleep-walking a rarest side effect of zolpidem. Indian journal of psychological medicine 2015; 37:105-106.

[47] Richey S M, Krystal A D. Pharmacological advances in the treatment of insomnia. Curr Pharm Des 2011; 17:1471-1475.

[48] Barrett J R, Tracy D K, Giaroli G. To sleep or not to sleep: a systematic review of the literature of pharmacological treatments of insomnia in children and adolescents with attention-deficit/hyperactivity disorder. Journal of child and adolescent psychopharmacology 2013; 23:640-647.

[49] Liu A, Tipton R, Pan W et al. Tart cherry juice increases sleep time in older adults with insomnia (830.9). The FASEB Journal 2014; 28:830.839.

[50] Vuong Q V, Bowyer M C, Roach P D. L-Theanine: properties, synthesis and isolation from tea. J Sci Food Agric 2011; 91:1931-1939.

[51] Weeks B S. Formulations of dietary supplements and herbal extracts for relaxation and anxiolytic action: Relarian. Medical science monitor: international medical journal of experimental and clinical research 2009; 15:RA256-262.

[52] Street R A, Sidana J, Prinsloo G. *Cichorium intybus*: Traditional uses, phytochemistry, pharmacology, and toxicology. Evidence-Based Complementary and Alternative Medicine 2013; 2013.

[53] Lyon M R, Kapoor M P, Juneja L R. The effects of L-theanine (Suntheanine) on objective sleep quality in boys with attention deficit hyperactivity disorder (ADHD): a randomized, double-blind, placebo-controlled clinical trial. Alternative medicine review: a journal of clinical therapeutic 2011; 16:348-354.

[54] Rao T P, Ozeki M, Juneja L R. In search of a safe natural sleep aid. Journal of the American College of Nutrition 2015; 34:436-447.

[55] Bannai M, Kawai N. New therapeutic strategy for amino acid medicine: glycine improves the quality of sleep. Journal of pharmacological sciences 2012; 118: 145-148.

[56] Udenigwe C C, Aluko R E. Food protein-derived bioactive peptides: production, processing, and potential health benefits. Journal of Food Science 2012; 77:R11-R24.

[57] Khiari Z, Ndagijimana M, Betti M. Low molecular weight bioactive peptides derived from the enzymatic hydrolysis of collagen after isoelectric solubilization/precipitation process of turkey by-products. Poultry science 2014; 93:2347-2362.

[58] Gómez-Guillén M, Giménez B, López-Caballero Ma, Montero M. Functional and bioactive properties of collagen and gelatin from alternative sources: A review. Food Hydrocolloids 2011; 25:1813-1827.

[59] Kim S-K, Ngo D-H, Vo T-S. Marine fish-derived bioactive peptides as potential antihypertensive agents. Adv Food Nutr Res 2012; 65:249-260.

[60] Cooper C A, Brown K K, Meletis C D, Zabriskie N. Inflammation and hyaluronic acid. Alternative & complementary therapies 2008; 14:78-84.

[61] Wesotowska A, Nikiforuk A, Michalska K et al. Analgesic and sedative activities of lactucin and some lactucin-like guaianolides in mice. Journal of ethnopharmacology 2006; 107:254-258.

[62] E I-Sayed Y S, Lebda M A, Hassinin M, Neoman S A. Chicory (*Cichorium intybus* L.) root extract regulates the oxidative status and antioxidant gene transcripts in CCl 4-induced hepatotoxicity. PloS one 2015; 10:e0121549.
[63] Aqil F, Ahmad I, Mehmood Z. Antioxidant and free radical scavenging properties of twelve traditionally used Indian medicinal plants. Turkish journal of Biology 2006; 30:177-183.

What is claimed:

1. A composition comprising:
   (a) a first component selected from one or more of the following: collagen, a gelatin peptide, or the amino acid glycine; wherein said first component has a molecular weight less than 3500 Dalton;
   (b) a second component comprising L-theanine;
   (c) a third component comprising lactucopicrin, deoxylactucopicrin, or another lactucopicrin derivative;
   (d) a fourth component comprising hyaluronic acid;
   (e) a fifth component comprising epigallocatechin gallate; and
   (f) a sixth component comprising quinic acid;
   wherein:
   said composition is supplied in aqueous solution or aqueous suspension, or said composition is supplied as a powder that can be reconstituted into an aqueous solution or an aqueous suspension; wherein the concentrations of the components of the aqueous solution or aqueous suspension are such that 30-60 mL of the aqueous solution or aqueous suspension supplies one dose that comprises: (i) 0.5 to 12 g collagen peptide, or 0.5 to 5 g glycine as amino acid; i.e., all or part of said first component; (ii) a tea (*Camellia sinensis*) extract containing 100 to 500 mg theanine, and 50 to 300 mg epigallocatechin gallate; i.e., all or part of said second and fifth components; and (iii) 1 to 10 g chicory (*Cichorium intybus*) extract containing lactucopicrin, deoxylactucopicrin, or another lactucopicrin; i.e., all or part of said third component;
   and wherein:
   said composition has the property that, if one dose of said composition is consumed orally by a human, one or more of the following will be improved: onset of sleep, sleep depth, sleep quality, sleep duration, sleep apnea, or fatigue during the waking part of the day.

2. The composition of claim 1, additionally comprising a nutritive sweetener.

3. A method for improving one or more of the following in a human: onset of sleep, sleep depth, sleep quality, sleep duration, sleep apnea, or fatigue during the day; said method comprising the human's orally consuming a dose of the composition of claim 1.

4. The composition of claim 1, additionally comprising a flavoring agent; wherein said flavoring agent comprises as least one flavoring component other than extract of tea (*Camellia sinensis*) and other than extract of chicory (*Cichorium intybus*).

5. The composition of claim 1, additionally comprising a non-nutritive sweetener.

* * * * *